[54] FURAN-3-CARBOHYDROXAMATES AND THEIR USE

[75] Inventors: Peter Neumann, Wiesloch; Michael Thomas, Weisenheim; Stefan Weiss, Neckargemuend; Hübert Traüth, Dudenhofen, all of Fed. Rep. of Germany

[73] Assignee: BASF Aktiengesellschaft, Ludwigshafen, Fed. Rep. of Germany

[21] Appl. No.: 673,784

[22] Filed: Nov. 21, 1984

[30] Foreign Application Priority Data

Nov. 23, 1983 [DE] Fed. Rep. of Germany ....... 3342219

[51] Int. Cl.$^4$ ...................... C07F 15/04; C07F 15/06
[52] U.S. Cl. .................................... 549/210; 549/487; 524/111
[58] Field of Search ............................... 549/210, 487

[56] References Cited

U.S. PATENT DOCUMENTS

| | | | |
|---|---|---|---|
| 2,787,621 | 4/1957 | Hook et al. ......................... | 549/210 |
| 3,733,348 | 5/1973 | Briggs et al. ....................... | 549/210 |
| 3,799,945 | 3/1974 | D'Amico ............................. | 549/210 |
| 3,993,772 | 11/1976 | Pommer et al. .................... | 549/487 |

Primary Examiner—Glennon H. Hollrah
Assistant Examiner—Dara Dinner
Attorney, Agent, or Firm—Oblon, Fisher, Spivak, McClelland & Maier

[57] ABSTRACT

Furan-3-carbohydroxamates of the formula

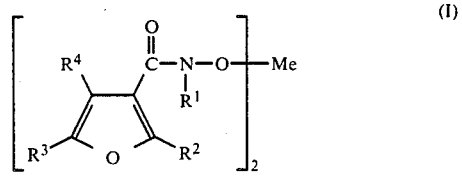

where $R^1$ is alkyl, unsubstituted or substituted cycloalkyl or unsubstituted or substituted phenyl, $R^2$ is methyl or ethyl, $R^3$ and $R^4$ independently of one another are each hydrogen, bromine, chlorine, unsubstituted or substituted alkyl, or —$CH_2$—$COOR^5$, where $R^5$ is unsubstituted or substituted alkyl, and Me is divalent nickel or cobalt, stabilize plastics against the action of light, oxygen and heat. The compounds (I) have only slight intrinsic color.

10 Claims, No Drawings

FURAN-3-CARBOHYDROXAMATES AND THEIR USE

The present invention relates to novel furan-3-carbohydroxamates and their use for stabilizing organic materials.

Organic materials, in particular plastics, which are sensitive to light, oxygen and heat are protected from external attack by stabilizers which are incorporated or applied as a protective layer.

Stabilizers for a very wide variety of uses have long been known.

It is an object of the present invention to provide, for thermoplastics, in particular polyolefins, stabilizers which possess little intrinsic color and have a good stabilizing action.

We have found that this object is achieved by the hydroxamates according to the invention.

The present invention relates to furan-3-carbohydroxamates of the formula

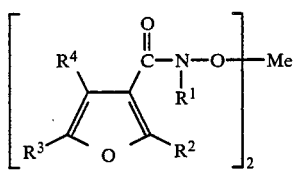

where $R^1$ is $C_1-C_{18}$-alkyl, $C_3-C_8$-cycloalkyl which is unsubstituted or monosubstituted or disubstituted by $C_1-C_4$-alkyl, or phenyl which is unsubstituted or monosubstituted, disubstituted or trisubstituted by $C_1-C_{12}$-alkyl, chlorine, bromine and/or $C_1-C_{12}$-alkoxy, the substituents being identical or different, $R^2$ is methyl or ethyl, $R^3$ and $R^4$ independently of one another are each hydrogen, bromine, chlorine, or $C_1-C_{18}$-alkyl which is unsubstituted or monosubstituted or disubstituted by chlorine, bromine and/or $C_1-C_4$-alkoxy, or are each $-CH_2-COOR^5$, where $R^5$ is $C_1-C_{18}$-alkyl which is unsubstituted or monosubstituted or disubstituted by chlorine, bromine and/or $C_1-C_4$-alkoxy, and Me is divalent nickel or cobalt.

The hydroxamates I stabilize plastics, e.g. thermoplastics, in particular polyolefins, such as polyethylene, polypropylene and other olefin homopolymers and copolymers, styrene homopolymers and copolymers, synthetic rubbers, polyvinylbutyral, ethylene/vinyl acetate copolymers, polyphenylene oxide and mixtures of these with other plastics, against the action of light, oxygen and heat. Another advantage is that, because (I) possesses little intrinsic color, the polymers are virtually unchanged in hue even when relatively high concentrations of (I) are used.

Specific examples of $C_1-C_{18}$-alkyl radicals $R^1$, $R^3$, $R^4$ and $R^5$ are methyl, ethyl, n-propyl, isopropyl, n-butyl, isobutyl, sec.-butyl, tert.-butyl, n-pentyl, 3-methylbutyl, 1-ethylpropyl, 1,1-dimethylpropyl, 2,2-dimethylpropyl, n-hexyl, n-heptyl, 1-ethylphenyl, n-octyl, 2-ethylhexyl, 2,4,4-trimethylpentyl, n-nonyl, n-decyl, n-undecyl, n-tridecyl, n-pentadecyl, n-heptadecyl and octadecyl.

Examples of suitable substituents on alkyl radicals $R^3$, $R^4$ and/or $R^5$ are chlorine, bromine, methoxy, ethoxy, 2-bromoethoxy, 2,2,2-trichloroethoxy and isobutoxy.

Specific examples of unsubstituted or alkyl-substituted cycloalkyl radicals $R^1$ are cyclopropyl, cyclobutyl, cyclopentyl, cyclohexyl, 4-methylcyclohexyl, 4-tert.-butylcyclohexyl, 3,5-dimethylcyclohexyl, cycloheptyl and cyclooctyl.

Examples of suitable unsubstituted or substituted phenyl radicals $R^1$ are phenyl, 2-, 3- and 4-methylphenyl, 2-, 3- and 4-ethylphenyl, 2-, 3- and 4-n-propylphenyl, 2-, 3- and 4-isopropylphenyl, 2-, 3- and 4-n-butylphenyl, 2-, 3- and 4-(but-2'-yl)-phenyl, 2-, 3- and 4-tert.-butylphenyl, 2,3-, 2,4-, 2,5-, 2,6-, 3,4- and 3,5-dimethylphenyl, 2,4,6-trimethylphenyl, 2,4-dimethyl-6-tert.-butylphenyl, n-hexylphenyl, heptylphenyl, octylphenyl, (2'-ethylhexyl)-phenyl, nonylphenyl, decylphenyl, dodecylphenyl, 2-, 3- and 4-chlorophenyl, 2-, 3- and 4-bromophenyl, 2,4-, 2,5-, 2,6- and 3,5-dichlorophenyl, 2-, 3-and 4-methoxyphenyl, 2-, 3- and 4-ethoxyphenyl, propoxyphenyl, n- and isobutoxyphenyl, hexyloxyphenyl, octyloxyphenyl, decyloxyphenyl, nonyloxyphenyl and dodecyloxyphenyl.

Preferred hydroxamates of the formula I are those in which $R^1$ is methyl, ethyl, cyclohexyl, phenyl, chlorophenyl or methylphenyl, $R^2$ and $R^3$ can be identical or different and are each methyl or ethyl, $R^4$ is hydrogen or methyl, and Me is divalent nickel.

Among these compounds I, noteworthy ones are those in which $R^1$ is phenyl, 4-chlorophenyl, 3-methylphenyl or cyclohexyl, $R^2$ and $R^3$ are each methyl, $R^4$ is hydrogen or methyl and Me is Ni. Very particularly preferred compounds (I) are those in which $R^1$ is phenyl or cyclohexyl, $R^2$ and $R^3$ are each methyl, $R^4$ is hydrogen and Me is Ni.

Because of its performance characteristics, the compound (I) in which $R^1$ is phenyl, $R^2$ and $R^3$ are each methyl, $R^4$ is hydrogen and Me is cobalt is also preferred.

The preparation of the hydroxamic acids from which the hydroxamates I are derived has been disclosed (German Laid-Open Application DOS No. 2,455,082). The metal salts are obtained by a conventional method, by reacting the hydroxamic acids with Me salts. The reaction is preferably carried out in polar water-miscible organic liquids, in particular methanol, ethanol or isopropanol, preferably ethanol.

Depending on the solvent used and/or the preparation conditions, the hydroxamate I may contain 1 mole or 2 moles of water of crystallization.

When used as stabilizers, the hydroxamates I are incorporated into the substances being stabilized, or are applied as a protective layer.

The concentration of (I) is from 0.05 to 2, preferably from 0.1 to 1.0, % by weight, based on the material being stabilized. Particularly suitable materials for stabilization are polyolefins, in particular polyethylene and polypropylene.

The skilled worker is familiar with the incorporation of (I) into the materials or the coating of these materials with (I), these operations being carried out by a conventional method (I) can also be incorporated together wth other stabilizers and, if required, other assistants conventionally employed in such materials.

The Examples which follow illustrate the invention. Parts are by weight.

A. Preparation of the hydroxamates

EXAMPLE 1

A warm solution of 26.15 parts of nickel (II) chloride hexahydrate in 50 parts of ethanol is added to 27.54 parts of potassium N-cyclohexyl-2,5-dimethylfuran-3-carbohydroxamate in 50 parts of ethanol at from 40 to 50° C. in the course of 15 minutes. The mixture is then stirred at this temperature for 4 hours, after which the precipitated potassium chloride is filtered off from the hot mixture, and the filtrate is evaporated down to half its volume under reduced pressure. When the filtrate concentrated in this manner is cooled, crystals separate out, and these are filtered off under suction and dried to give 24.8 parts of the nickel salt of the formula

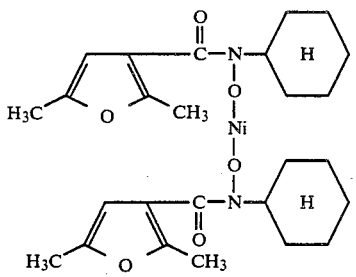
(II)

of melting point 120°–128° C.

EXAMPLES 2 to 4

The procedure described to Example 1 is followed, except that the potassium salts of the hydroxamic acids stated in the Table are used. After the working up procedure, the nickel salt of the hydroxamic acid III is obtained in the amount shown in column 4 and with the melting point given in column 5.

(III)

| Example | Hydroxamic acid (III) Potassium salt [parts] | Y | Nickel hydroxamate Yield [parts] | mp. [°C.] |
|---|---|---|---|---|
| 2 | 26.94 | –⌬ | 24.1 | 270 |
| 3 | 30.39 | –⌬–Cl | 27.3 | 164/168 |
| 4 | 28.34 | –⌬–CH₃ | 25.5 | 220/224 |

EXAMPLE 5

A warm solution of 26.17 parts of cobalt (II) chloride hexahydrate in 50 parts of ethanol is added to 27.54 parts of potassium N-cyclohexyl-2,5-dimethylfuran-3-carbohydroxamate by a procedure similar to that described in Example 1, and the mixture is worked up. Yield: 24.3 parts of the cobalt hydroxamate of the formula

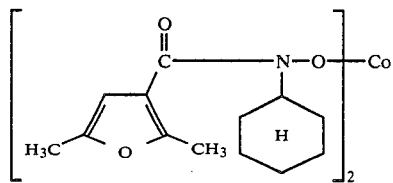
(IV)

mp. 59°/67° C.

B. Use Examples

USE EXAMPLE 1

(a) 0.25 part of the compound from Example 1 is incorporated into 100 parts of polyethylene powder by extruding twice at 180° C., and the material is pressed to give 200 μm thick sheets. After storage in the dark for 14 days at 25° C., the surface of the sheets does not exhibit any coating.

(b) The resistance to weathering of the sheets produced as described in (a) is tested in a Q.U.V. apparatus. The aging is determined by measuring the CO number after defined time intervals. The results of the measurement are summarized in the Table below.

(c) Comparison with the prior art

Pressed polyethylene sheets containing 0.25% of n-butylamine-nickel 2,2'-thiobis(4-tert.-octylphenolate) are weathered as described in (b). The results are summarized in the Table below.

| Use Example | CO number Weathering time [hours] | | | | |
|---|---|---|---|---|---|
| | 0 | 500 | 1000 | 1500 | 2000 |
| 1b | 0.2 | 0.25 | 1.3 | 5.4 | 7.55 |
| 1c | 0.2 | 0.25 | 0.4 | 1.3 | 8.25 |

USE EXAMPLE 2

0.25 part of the compound from Example 2 is incorporated into 100 parts of polypropylene powder by extruding twice at 180° C., and the material is pressed to give 200 μm thick sheets. After storage in the dark for 14 days at 25° C., the surface of the sheets does not exhibit any coating.

We claim:

1. A furan-3-carbohydroxamate of the formula:

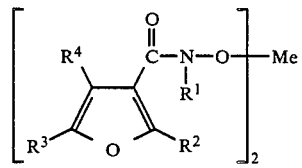

wherein $R^1$ is $C_1$–$C_{18}$-alkyl, $C_3$–$C_8$-cycloalkyl which is unsubstituted or monosubstituted or disubstituted by $C_1$–$C_4$-alkyl, or phenyl which is unsubstituted or monosubstituted or disubstituted or trisubstituted by identical or different substituents selected from the group consisting of $C_1$–$C_{12}$ alkyl, chlorine, bromine or $C_1$–$C_{12}$ alkoxy, $R^2$ is methyl or ethyl, $R^3$ and $R^4$ independently of one another are each hydrogen, bromine, chlorine, or $C_1$–$C_{18}$-alkyl which is unsubstituted or monosubstituted or disubstituted by chlorine, bromine or $C_1$–$C_4$-alkoxy, or are each —CH$_2$—COOR$^5$, where R$^5$ is C$_1$–C$_{18}$-alkyl which is unsubstituted or monosubstituted or disubstituted by chlorine, bromine or C$_1$–C$_4$-alkoxy, and Me is divalent nickel or cobalt.

2. A furan-3-carbohydroxamate as claimed in claim 1, wherein R$^1$ is methyl, ethyl, cyclohexyl, phenyl, chlorophenyl or methylphenyl, R$^2$ and R$^3$ independently of one another are each methyl or ethyl, R$^4$ is hydrogen or methyl, and Me is divalent nickel.

3. A furan-3-carbohydroxamate of the formula

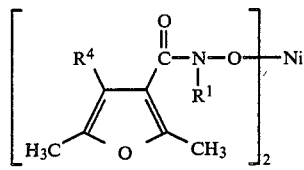

where R$^1$ is phenyl, 4-chlorophenyl, 3-methylphenyl or cyclohexyl and R$^4$ is hydrogen or methyl.

4. A furan-3-carbohydroxamate as claimed in claim 3, wherein R$^4$ is hydrogen.

5. A furan-3-carbohydroxamate as claimed in claim 3, wherein R$^1$ is phenyl or cyclohexyl, and R$^4$ is hydrogen.

6. A furan-3-carbohydroxamate as claimed in claim 3, wherein R$^1$ is phenyl, and R$^4$ is hydrogen.

7. A furan-3-carbohydroxamate as claimed in claim 3, wherein R$^1$ is cyclohexyl, and R$^4$ is hydrogen.

8. A furan-3-carbohydroxamate as claimed in claim 1, of the formula

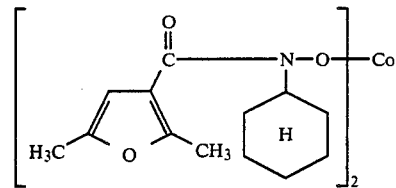

9. A furan-3-carbohydroxamate as claimed in claim 1, wherein said C$_1$–C$_{18}$-alkyl radicals of R$^1$, R$^3$, R$^4$ and R$^5$ are methyl, ethyl, n-propyl, isopropyl, n-butyl, isobutyl, sec.-butyl, tert.-butyl, n-pentyl, 3-methylbutyl, 1-ethylpropyl, 1,1-dimethylpropyl, 2,2-dimethylpropyl, n-hexyl, n-heptyl, 1-ethylphenyl, n-octyl, 2-ethylhexyl, 2,4,4-trimethylpentyl, n-nonyl, n-decyl, n-undecyl, n-tridecyl, n-pentadecyl, n-heptadecyl and octadecyl.

10. A furan-3-carbohydroxamate as claimed in claim 1, wherein said substituted phenyl radical R$^1$ is 2-, 3- and 4-methylphenyl, 2-, 3- and 4-ethylphenyl, 2- , 3- and 4-n-propylphenyl, 2-, 3- and 4-isopropylphenyl, 2-, 3- and 4-n-butylphenyl, 2-, 3- and 4-(but-2'-yl)-phenyl, 2-, 3- and 4-tert.-butyl-phenyl, 2, 3-, 2, 4-, 2, 5-, 2, 6-, 3, 4- and 3,5-dimethylphenyl, 2,4,6-trimethylphenyl, 2,4-dimethyl-6-tert.-butylphenyl, n-hexylphenyl, heptylphenyl, octylphenyl, (2'-ethylhexyl)-phenyl, nonylphenyl, decylphenyl, dodecylphenyl, 2-, 3- and 4-chlorophenyl, 2-, 3- and 4-bromophenyl, 2,4-, 2,5- 2,6- and 3,5-dichlorophenyl, 2-, 3- and 4-methoxyphenyl, 2-, 3- and 4-ethoxyphenyl, propoxyphenyl, n- and isobutoxyphenyl, hexyloxyphenyl, octyloxyphenyl, decyloxyphenyl, nonyloxyphenyl and dodecyloxyphenyl.

* * * * *